United States Patent [19]

Abbatte et al.

[11] Patent Number: 4,755,139
[45] Date of Patent: Jul. 5, 1988

[54] ORTHODONTIC ANCHOR APPLIANCE AND METHOD FOR TEETH POSITIONING AND METHOD OF CONSTRUCTING THE APPLIANCE

[75] Inventors: Gerard P. Abbatte, Buffalo; John J. Cunat, Snyder, both of N.Y.

[73] Assignee: Great Lakes Orthodontics, Ltd., Tonawanda, N.Y.

[21] Appl. No.: 8,347

[22] Filed: Jan. 29, 1987

[51] Int. Cl.$^4$ ............................................... A61C 7/00
[52] U.S. Cl. ........................................................ 433/6
[58] Field of Search ...................................... 433/6, 24

[56] References Cited

U.S. PATENT DOCUMENTS

| | | |
|---|---|---|
| 2,467,432 | 4/1949 | Kesling . |
| 2,531,222 | 11/1950 | Kesling . |
| 4,055,895 | 11/1977 | Huge . |
| 4,073,061 | 2/1978 | Bergersen . |
| 4,371,336 | 2/1983 | Hilleman . |
| 4,433,956 | 2/1984 | Witzig ..................................... 433/7 |

Primary Examiner—Robert Peshock
Attorney, Agent, or Firm—Christel, Bean & Linihan

[57] ABSTRACT

An orthodontic anchor appliance for repositioning anterior teeth of a dental patient includes a relatively hard splint portion for securement to preselected ones of the patient's posterior teeth positioned on opposite sides of the dental arch containing the anterior teeth desired to be repositioned and an elastic positioner portion joined to the splint portion for urging the anterior teeth to a preselected position. Both the splint portion and positioner portion are formed from appropriate materials which are pliable when a pre-hardened or pre-cured condition and are applied to and shaped about a diagnostic model of the patient's arch containing portions simulating the anterior teeth when positioned in the preselected position. When the appliance is operatively positioned within the mouth, the splint portion is closely fitted about and thereby anchored to the posterior teeth and the elastic positioner portion is closely fitted, about, in a flexed or deformed condition, about the anterior teeth. In the flexed condition, the elastic positioner portion acts between the anchored splint portion and the anterior teeth to urge the anterior teeth to the preselected position.

19 Claims, 2 Drawing Sheets

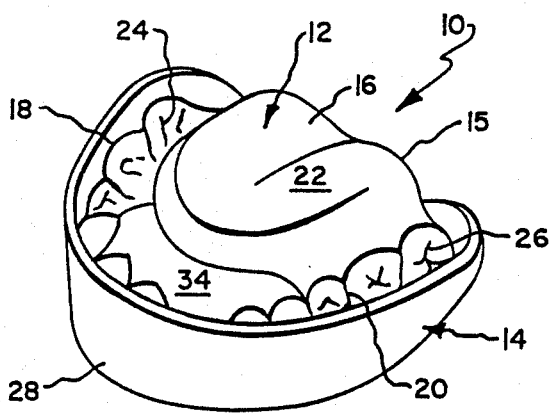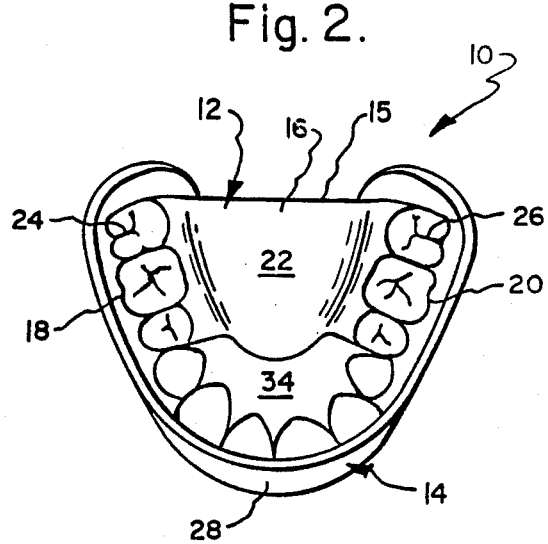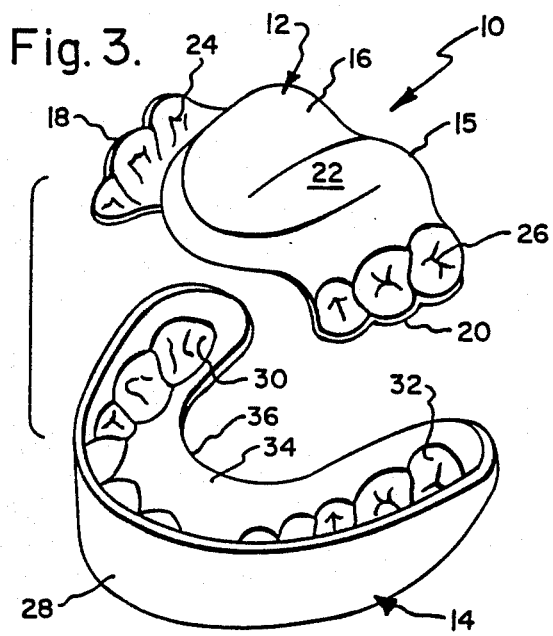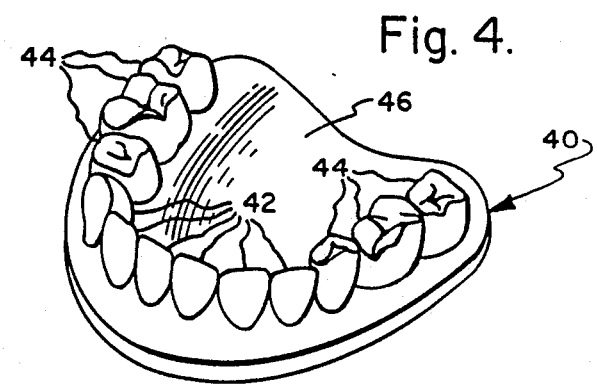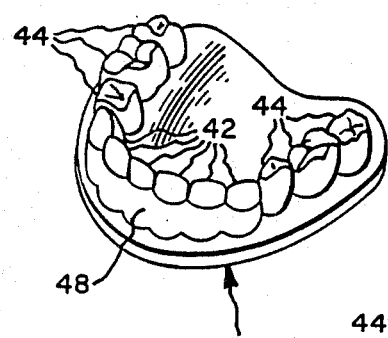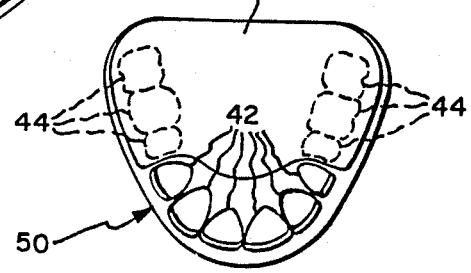

ORTHODONTIC ANCHOR APPLIANCE AND METHOD FOR TEETH POSITIONING AND METHOD OF CONSTRUCTING THE APPLIANCE

BACKGROUND OF THE INVENTION

This invention relates generally to the orthodontic treatment of teeth and relates more particularly to an orthodontic appliance for urging teeth toward a preselected orientation.

The type of orthodontic appliance to which the apparatus of this invention is to be compared includes an elastic preform or positioning portion defining a teeth-receiving trough adapted to closely accept at least a portion of a row of upper or lower teeth of a patient's mouth and possessing a degree of elasticity for urging predetermined ones of the closely-accepted teeth toward a desired position. An example of such an appliance, or tooth positioner, is shown and described in U.S. Pat. No. 3,407,500.

Conventional positioners which each include an elastic preform commonly also include anchor means for anchoring the preform to the teeth. The anchor means of the positioner of the referenced patent, for example, includes a coupling arrangement having a first rigid member supported by the preform and a second rigid coupling member mounted upon the teeth and which cooperates with the first rigid coupling member for anchoring the preform to the teeth.

It is an object of the present invention to provide a new and improved anchor appliance including an elastic preform or positioner portion for urging teeth toward a preselected position and a method of constructing and using the appliance.

Another object of the present invention is to provide such an appliance including improved means for anchoring the elastic positioner portion within a patient's mouth.

Still another object of the present invention is to provide such an appliance which can be comfortably worn within the mouth and which can be easily positioned within and removed from the mouth.

Yet still another object of the present invention is to provide such an appliance which is economical to construct and effective in operation.

SUMMARY OF THE INVENTION

This invention resides in a new and improved orthodontic anchor appliance for repositioning anterior teeth of a patient and a method of constructing and using the anchor appliance.

The anchor appliance includes a relatively hard splint portion and an elastic positioner portion joined to the splint portion. The splint portion is securable to preselected ones of the posterior teeth of the patient positioned on opposite sides of the mouth and arranged in the corresponding one of the upper or lower dental arch containing the anterior teeth desired to be repositioned. The elastic positioner portion is securable when in a flexed condition to preselected ones of the anterior teeth when the appliance is operatively positioned within the mouth of a patient so that the elastic positioner portion acts between the splint portion and the anterior teeth to urge the anterior teeth toward a preselected position.

A method of repositioning anterior teeth of a patient includes the steps of providing the appliance of this invention and positioning the appliance within the patient's mouth so that the splint portion is operatively secured to the posterior teeth and the elastic positioner portion is operatively secured to the anterior teeth. With the appliance fitted within the mouth as aforesaid, the elastic positioner portion acts between the splint portion and the anterior teeth to urge the anterior teeth toward a preselected position.

The steps involved in constructing the anchor appliance of the invention include an initial step of forming a dental model from an impression taken of the patient's dental arch containing the anterior teeth desired to be repositioned. The portions of the dental model simulating the anterior teeth are then positioned to a preselected position so as to provide a diagnostic model of the patient's dental arch when the anterior teeth therein are oriented in a preselected position. A hardenable material, when in a pliable condition, is shaped in conformity with portions of the diagnostic model so that a first part of the pliable, hardenable material conforms to the shape of a preselected one of the patient's posterior teeth positioned on one side of the dental arch, a second part of the pliable, hardenable material conforms to the shape of a preselected one of the patient's posterior teeth positioned on the other side of the dental arch and a third part of the pliable, hardenable material joins the first and second parts and conforms to the shape of mouth tissue extending between the preselected posterior teeth positioned on opposite sides of the dental arch. The hardenable material is then permitted to harden to form the splint portion of the appliance. A curable elastomeric material, when in a pliable condition, is then shaped in conformity with at least a section of the splint portion and a portion of the diagnostic model simulating the repositioned anterior teeth. The elastomeric material is thereafter permitted to cure to a resiliently flexible condition so as to form the elastic positioner portion of the appliance. When the appliance is operatively positioned within the mouth of the patient so that the splint portion is closely fitted about the preselected ones of the posterior teeth and the positioner portion is closely fitted in a flexed condition about the preselected ones of the anterior teeth, the splint portion is firmly anchored to the posterior teeth and the positioner portion acts between the splint portion and anterior teeth to urge the anterior teeth toward the preselected position.

BRIEF DESCRIPTION OF THE DRAWING FIGURES

FIG. 1 is a perspective view of an embodiment of an anchor appliance in accordance with the apparatus of the present invention.

FIG. 2 is a plan view of the FIG. 1 appliance as seen generally from above in FIG. 1.

FIG. 3 is a perspective view, shown exploded, of the FIG. 1 appliance.

FIG. 4 is a perspective view of a study model of a patient's upper dental arch used to form the appliance of this invention.

FIG. 5 is a perspective view of a diagnostic model constructed from the FIG. 4 study model.

FIG. 6 is a perspective view of the FIG. 5 diagnostic model shown with a hardenable material being applied to preselected portions of the FIG. 5 model.

FIG. 7 is a plan view of the diagnostic model and material of FIG. 6 as seen from above in FIG. 6.

DETAILED DESCRIPTION OF THE ILLUSTRATED EMBODIMENTS

Figure 8:
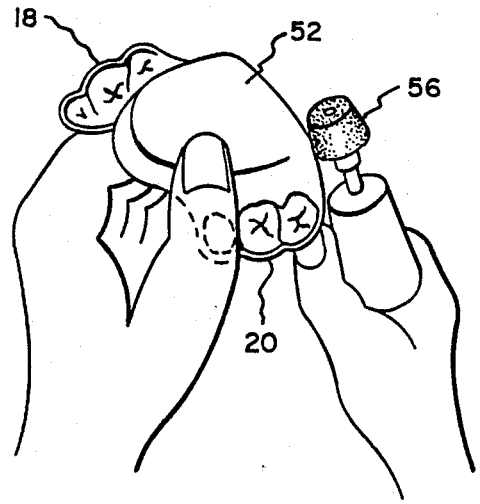
FIG. 8 is a perspective view of the splint portion of the appliance being finished to a desired shape.

Turning now to the drawings in greater detail and considering first FIGS. 1–3, there is shown an orthodontic anchor appliance, generally indicated 10, in accordance with the apparatus of this invention. The appliance 10 is of such size and shape to be operatively positioned within the mouth of a patient and fitted about the teeth of the patient's maxillary, or upper, dental arch. When operatively worn within the patient's mouth and as will be explained in greater detail hereinafter, the appliance 10 acts between preselected ones of the posterior teeth of the maxillary arch and the anterior teeth thereof to urge the anterior teeth toward a preselected position or orientation and to thereby alter the position of the anterior teeth relative to the posterior teeth.

The appliance 10 includes a relatively hard splint portion 12 for anchoring the appliance 10 to the posterior teeth and an elastomeric positioner portion 14 joined to the splint portion 12. The splint portion 12 is in the form of a relatively thin body 15 which is securable to preselected ones of the posterior teeth of the patient, which teeth are positioned on opposite sides of the maxillary arch, and adapted to fit comfortably within the mouth when worn. To this end, the body of the splint portion 12 includes a tissue-engaging body part 16 and two teeth-engaging body parts 18,20 joined to opposite sides of the tissue-engaging part 16.

The tissue-engaging part 16 is of such size as to extend from one side of the maxillary arch to the other and defines a roof-engaging surface 22 shaped generally complementary to the roof of the patient's mouth. Therefore, when the appliance 10 is operatively positioned within the mouth, the tissue-engaging part 16 comfortably engages the roof of the mouth.

With reference still to FIGS. 2 and 3, each teeth-engaging part 18 or 20 defines a recessed surface 24 or 26, respectively, shaped generally complementary to the crowns of the corresponding posterior teeth to which the teeth-engaging part 18 or 20 is securable. Therefore, when teeth-engaging parts 18,20 are pressed upon so as to be fitted about the preselected posterior teeth, the posterior teeth are closely received by the recessed surfaces 24,26 to anchor the appliance 10 to the posterior teeth. In the appliance embodiment 10 illustrated in FIGS. 1–3, the recessed surfaces 24 or 26 of the teeth-engaging part 18 or 20 are shaped complementary to that of the bicuspids and first and second molars of the patient, which bicuspids and molars are positioned on opposite sides of the patient's maxillary arch and positioned in a desired or satisfactory condition relative to the desired arrangement of teeth in the maxillary arch.

The splint portion 16 is constructed of such known dental materials as a thermoformed dental plastic or a light, heat or autopolymerizing dental resin, each of which is hardenable during formation of the splint portion 16 from a pliable condition to a relatively stiff, hardened condition. Examples of materials suitable for forming the splint portion 12 are designated by the trademark Splint Biocryl II and the trademark Splint Resin and are each available from Great Lakes Orthodontics, Ltd., Buffalo, N.Y. Splint Biocryl II is a clear thermoformable plastic available in sheets from Eastman Chemical Corporation and is also known as Kodar PETG Copolyester. Splint Resin is a two-component mixture of an acrylic Polymer supplied in powder form and Methylmethacrylate Monomer supplied in liquid form. The liquid/powder mixture of Splint Resin self-cures into a clear plastic. In its hardened or cured condition, splint portion 16 is of sufficient rigidity to strongly resist deformation.

With reference still to FIGS. 2 and 3, the positioner portion 14 is in the form of an arcuate body 28 resembling a mouthguard including opposite end sections 30,32 and a teeth-engaging section 34 positioned between the end sections 30,32. As best shown in FIG. 1, the teeth-engaging parts 18,20 of the splint portion 12 and the end sections 30,32 of the positioner portion 14 are so shaped as to suitably mesh or mate when operatively placed or pressed in overlying relationship with one another so that the appliance 10 can be worn as a two-layered appliance with no need for adhesive applied therebetween. In such an embodiment, the splint and positioner portions are releasably joined by the mated or meshed relationship therebetween so that the appliance 10 can be pulled apart and thereby disassembled for purposes such as, for example, cleaning each of the splint portion 16 and the positioner portion 14. To provide a permanent bond between the splint and positioner portions 12 and 14, a suitable glue or adhesive can be applied so as to be positioned between the engaging surfaces of the positioner end sections 30,32 and the anchor teeth-engaging parts 18,20.

The teeth-engaging section 34 of the positioner portion 28 defines an indented surface 36 which extends generally along the arc of the body 28. The indented surface 36 is shaped generally complementary to the crowns of the anterior teeth of the maxillary arch when the anterior teeth are positioned in a preselected or desired position or orientation.

The positioner portion 14 may be constructed of any of various elastomers such as liquid injection molded silicone elastomer, a hand laid up silicone elastomer, thermoformed elastomers, mixed compression molded elastomers or injection molded elastomers. Characteristically, the material comprising the positioner portion 28 is pliable when in an uncured condition and is curable to a condition possessing a degree of flexibility, elasticity, and resilience so that if the positioner portion 28 is flexed or deformed from a relaxed or undeformed condition, the memory of the positioner portion 28 tends to return the positioner portion 28 to or resume the shape possessed when in its undeformed condition.

Specific examples of material out of which the positioner portion 28 can be constructed are designated by the trademarks Bioplast available from Scheu-Dental, West Germany, and Silastic Q7-4840 and Silastic MDX-4-4515 each of which is available from Dow Corning Corp., Midland, Mich. Bioplast is a thermoformable vinyl supplied in sheets, and Silastic Q7-4840 is comprised of two viscous pastes which when mixed in equal volumes and heat-cured will vulcanize into a generally clear silicone rubber of about Shore A 40 Durometer. Silastic MDX-4-4515, also known as Silicone Rubber GL0441 and available from Great Lakes Orthodontics, Ltd, is a pre-blended mixture which remains uncured while refrigerated and is hand workable at room temperature. After hand working, the mixture of Silastic MDX-4-4515 is heat cured to a vulcanized silicone rubber which is generally clear and has a Shore A Durometer of 50.

When operatively positioned within the mouth of the patient, the appliance 10 is closely fitted about the teeth of the maxillary arch so that the teeth-engaging parts 18, 20 of the splint portion 12 are fitted about the patient's bicuspids and molars and the teeth-engaging section 34 of the positioner portion 14 is forced upon so as to be fitted about the anterior teeth of the arch. When the appliance 10 is placed in such an operative position, the tissue-engaging part 16 of the splint section 12 lies in substantial conformity with the roof of the patient's mouth, and it is believed that the resulting engagment between the tissue-engaging part 16 and the mouth tissue (i.e., the roof of the mouth) contribute to the anchoring of the splint portion 16 in a stationary position within the mouth. It will be understood that because the indented surface 36 of the positioner portion 14 is shaped in conformity to the anterior teeth when positioned in the preselected orientation and the splint portion 12 is anchored to the patient's posterior teeth, the operative positioning of the teeth-engaging section 34 of the positioner portion 14 upon the patient's anterior teeth necessitates a deformation or flexing of the positioner portion 14 about the anterior teeth. Due to the deformed condition of the positioner portion 14 about the anterior teeth, the positioner portion 14 effectively urges the anterior teeth toward the preselected position or orientation as the resiliency of the positioner portion urges the return of the positioner portion 14 to an undeformed condition. Hence, the appliance 10 applies orthodontic force between the posterior and anterior teeth to push the anterior teeth to a preselected orientation.

It has been found that anchor appliances similar in construction to that of appliance 10 of FIGS. 1–3 can be so designed to elicit any of several readjustments of the patient's teeth such as the orthodontic retraction and alignment of spaced anterior teeth, protraction and alignment of crowded anterior teeth, or rotation, tipping or translatory movement of anterior teeth.

In order to construct the appliance 10 and with reference to FIG. 4, a dental model 40 is initially formed from an impression taken from the maxillary arch of the patient. Model 40, also known in the art as a study model, is formed according to conventional procedures which are readily known to those skilled in the art so the detailed description thereof is believed to be unnecessary. Suffice it to say, the dentist or orthodontist takes an impression of the patient's teeth by having the patient bite into a suitable material capable of retaining an impression and then the impression-retaining material is used as a mold to form the model 40 of plaster or other suitable model material. Model 40 thus provides a facsimile of the upper jaw of a patient including anterior teeth 42, posterior teeth 44 and a palatal surface portion 46 conforming to the roof of the patient's mouth. In the model 40, the anterior teeth 42 include the incisors and cuspids, and the posterior teeth 44 include the bicuspids and first and second molars.

The next step in the construction process is to reposition portions of the FIG. 4 dental model 40 simulating the anterior teeth 42 to desired or preselected position. Commonly, the preselected positions will correspond to the ideal or orthodontist-prescribed positions of the anterior teeth 42. To reposition the anterior teeth-simulating portions and with reference to FIG. 5, the anterior teeth 42 of the dental model 40 are separated from the remainder of the model and reaffixed thereto with the teeth oriented in the preselected orientation. Commonly, a sharp knife (not shown) or similar tool suitable for cutting plaster is used to cut and thereby separate each anterior tooth from the remainder of the model 40. A suitable wax, indicated 48, is used to reaffix the teeth 42 to the remainder of the model 40. More specifically, the wax 48 is applied to the model 40 in the region thereof from which the anterior teeth 42 were cut, and the anterior teeth 42 are reset in the wax 48 in the preselected orientation or position. The resultant dental model, commonly referred to as a diagnostic model and indicated 50 in FIG. 5, thus provides a facsimile of the upper jaw of the patient with the anterior teeth 42 therein arranged in a desired orientation.

The splint portion 12 of the appliance 10 is then formed by shaping a suitable hardenable material in conformity with portions of the diagnostic model 50. More specifically, a hardenable material, indicated 52 and when in a pliable condition, is applied to portions of the diagnostic model 50 simulating the palate 46 and preselected ones of the posterior teeth 44 and shaped about the pliable hardenable material 52 to conform the material to the shape of the palate 46 and the posterior teeth 44. The specific steps involved in the application and/or shaping of the splint portion material 52 depend largely upon the type of material 52 applied to the model 50. For example, if the material 52 is a dental thermoplastic material which is pliable when heated to an elevated temperature and which is relatively hard and rigid when cooled from the elevated temperature to, for example, about 100° F., the thermoplastic material is shaped about the diagnostic model 50 when in a heated condition. The shaping of the thermoplastic material can be carried out by a process in which air pressure is applied to the heated material for effectively forming the material to the contour of portions of the model, or more specifically, the model portions simulating the palatal surface 46 and posterior teeth 44. When subsequently cooled, the hardened thermoplastic material 52 retains the contours of the palatal surface 46 and posterior teeth 44.

An apparatus for shaping heated thermoplastic material, such as the aforementioned Splint Biocryl II, about portions of the model as aforedescribed is available under the commercial designation BIOSTAR Dental Molding Machine from Great Lakes Orthodontics, Ltd., Tonawanda, N.Y. Briefly, a shaping operation performed with the BIOSTAR machine includes the placing of a thermoplastic blank over desired portions of the model 50, heating the plastic blank to a softened condition with the use of a heater lamp mounted in the machine, and applying air pressure to the softened blank to form the plastic to the contour of the desired portions of the model 50.

By way of further example, if the material 52 of the splint portion 12 is comprised of a polymerized dental resin consisting of a mixture of known resin compositions requiring light, heat or prescribed amount of time to cure, the resin compositions are applied to and shaped about the diagnostic model 50 and cured according to the requirement of the compositions. As shown in FIG. 6, these known resin compositions can be applied to and shaped about the model 50 by means of the fingers F, as shown or with a suitable applicator/shaping tool. In any event, however, the splint portion 12 is comprised of a hardenable material adapted to transform from a pliable condition suitable for shaping purposes to a hardened condition for resisting deformation upon the occurrence of a predetermined event such as a drop in temperature of the material 52, the application of sufficient light or heat or the appropriate passage of time.

The patient's posterior teeth to which the appliance 10 is anchored commonly are not moved during efforts to reposition anterior teeth with the appliance 10. Hence, it is desirable that the posterior teeth to which the appliance 10 is anchored be positioned in a desired or satisfactory condition. Therefore, when selecting the posterior teeth to which the appliance 10 is to be anchored, consideration is given to the actual positioning of the posterior teeth in relationship to the desired or ideal positioning thereof, and the splint portion 12 is preferably formed about the posterior teeth which are positioned in a satisfactory position during construction of the appliance 10.

Once the splint material 52 is cured to a hardened condition, and with reference to FIG. 8, the hardened material 52 is removed from the model 50 for finishing purposes. To finish the hardened material 52 and thereby form the splint portion 12, the material 52 can be trimmed or ground with a hand-held grinding tool 56 as shown in FIG. 8 or trimmed with an alternative tool, such as a cutting bur to the desired peripheral shape. Trimmed edges are then polished to a smooth condition.

It has been found that removal of the splint portion from the diagnostic model may damage the diagnostic model 50 to the extent that it cannot be reused. Inasmuch as the elastic positioner portion 14 of the appliance 10 is necessarily formed in the manner described hereinafter from the contours of the diagnostic model 50 subsequent to the formation of the splint portion 12, it is necessary to have available an undamaged diagnostic model for the formation of the positioner portion 14. Therefore, it is preferred that following the formation of the diagnostic model 50, a second, or duplicate, diagnostic model (not shown) be constructed for the purposes of forming the positioner portion 14. The second diagnostic model can be formed from an alginate impression made of the first diagnostic model 50 and then the impression used as a mold to form a second diagnostic model constructed entirely of plaster or equivalent material.

Once the splint portion 12 has been finished as desired, it is replaced upon the diagnostic model 50, or a duplicate thereof, and an elastomeric material is shaped in conformity with at least a section of the splint portion 12 and a portion of the diagnostic model simulating the repositioned anterior teeth. In accordance with an embodiment of the method of this invention and with reference to FIG. 9. an elastomeric material, indicated 60, out of which the positioner portion 14 is formed is applied to the diagnostic model 50 so as to overlie the teeth engaging parts 18,20 of the splint portion 12 and the anterior teeth-simulating portion 42 of the model 50 and shaped thereabout so that the material 60 conforms to the shape of the teeth-engaging parts 18,20 and the anterior teeth 42. As mentioned above, the material 60 of the positioner portion 14 can be any of several types of elastomers and as is the case with the splint portion material 52, the specific steps involved to shape the postioner portion material 60 in conformity with a section of the splint portion 12 and a portion of the diagnostic model depend largely upon the type of material 60 used to form the postioner 14. For example, if the positioner portion material 60 is a thermoformed elastomer, the material 60 is applied to the splint portion 12 and model 50 and shaped thereabout in a heated, softened condition. The shaping of the theroformed elastomer can be carried out by the application of mechanical vacuum or pressure or hand forming the elastomer about the splint portion 12 and model 50. The softened thermoformed elastomer is subsequently cured by cooling the material 60.

The aforementioned material Bioplast out of which the elastic positioner portion 14 can be formed has been found to be compatable with the aforementioned BIOSTAR Dental Molding Machine in that the Bioplast material, in the form of the thermoformable vinyl sheet, can be placed over the model 50 and splint portion 16 and shaped with the BIOSTAR machine to form the vinyl to the contour of the desired portions of the model 50 and splint portion 12.

If the material out of which the positioner portion 14 is formed is Silastic MDX-4-4515, the material can be applied with the fingers to the model 50 in the form of uncured strips and shaped with the fingers. Such application and shaping with the fingers is commonly referred to as a hand laid up technique. Once shaped as desired, the material can be smoothed with a suitable smoothing object, such as a melting ice cube.

Figure 12:
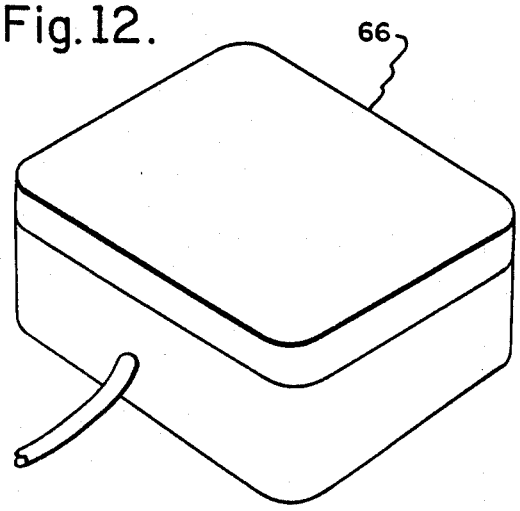
FIG. 12 is a perspective view of a mold in which the positioner portion of the appliance is formed in accordance with one embodiment of the method of this invention.
Figure 13:
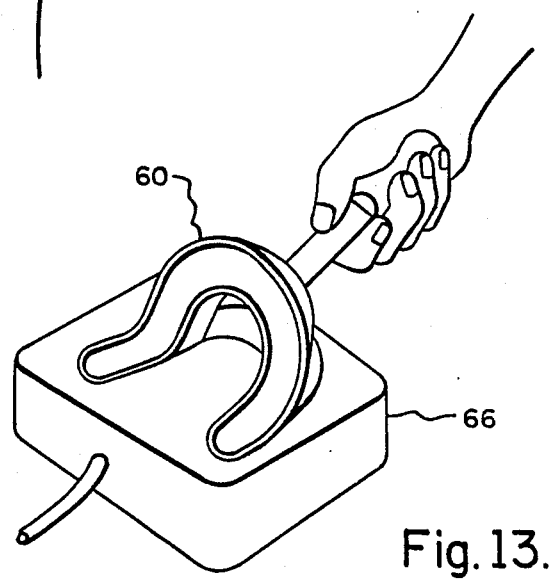
FIG. 13 is a perspective view of a positioner portion being removed from the FIG. 14 mold.

Furthermore and with reference to FIGS. 12 and 13, if the positioner portion material 60 is a liquid injection molded silicone elastomer, the step of applying and shaping the material 60 is preceded by the steps of forming a pattern for the elastic positioner portion 14 in wax over the preselected portions of the splint portion 12 and model 50, investing the pattern in an ejection type flask 66, boiling out the wax, injecting and vulcanizing the silicone elastomer and then removing the cured elastomer as shown in FIG. 13. The aforementioned material Silastic Q7-4840 can be used to injection mold the positioner portion 14.

Figure 9:
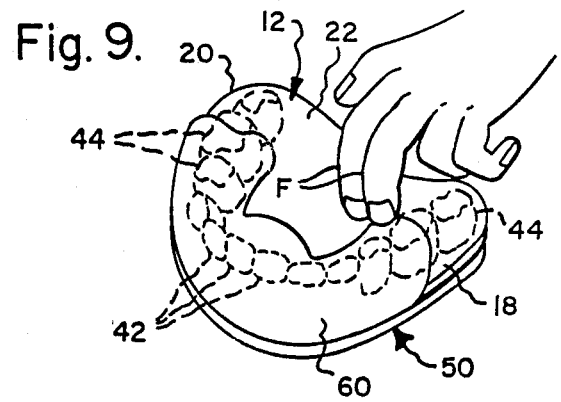
FIG. 9 is a plan view similar to that of FIG. 6 illustrating the finished splint portion repositioned upon the diagnostic model and elastomeric material being applied to and shaped about preselected portions of the diagnostic model and splint portion.
Figure 10:
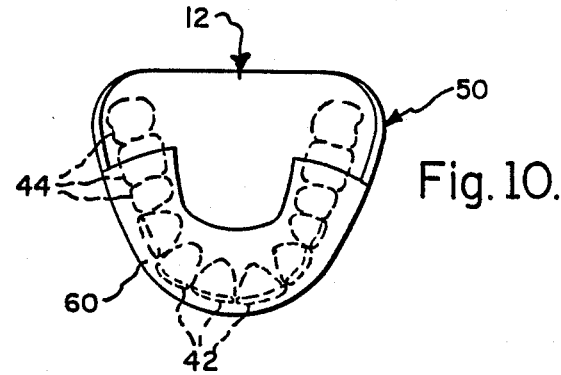
FIG. 10 is a plan view of the model and material of FIG. 9 as seen from above in FIG. 9.

Still further and as illustrated in FIG. 9, if the positioner portion material 60 is a premixed silicone elastomer, the elastomer can be simply applied by hand to the splint portion 12 and model 50 with a spatula 62 and the positioner portion 14 formed by the build up of elastomer. The shaping of the elastomer is effected as it is built up. Yet still further, if the positioner portion material 60 is a mixed elastomer, the positioner portion 14 can be formed about the splint portion 12 and model 50 by compression or injection molding techniques.

In any event, the positioner portion material 14 is shaped in conformity to the shape of the model 50 and splint portion 12 as the contours of the model 50 and splint portion 12 provide the standard for the formation of the contours of the positioner portion.

Once the elastic positioner portion material 60 is formed to the desired shape, it is permitted to cure according to the curing requirements of the material composition so that the cured material possesses a degree of flexibility and elasticity. For example, if the positioner portion material 60 is a thermoformed elastomer which when heated is pliable and when subsequently cools to a cured condition, the material 60 is simply permitted to cool to the hardened condition. Other elastomers which are well-suited as a positioner portion material 60, such as an injection molded elastomer, require a prescribed amount of time to cure. In any event, the curing of the positioner portion material 14 involves the occurrence of a predetermined event such as a drop in temperature of the material 60 or the passage of time.

Figure 11:
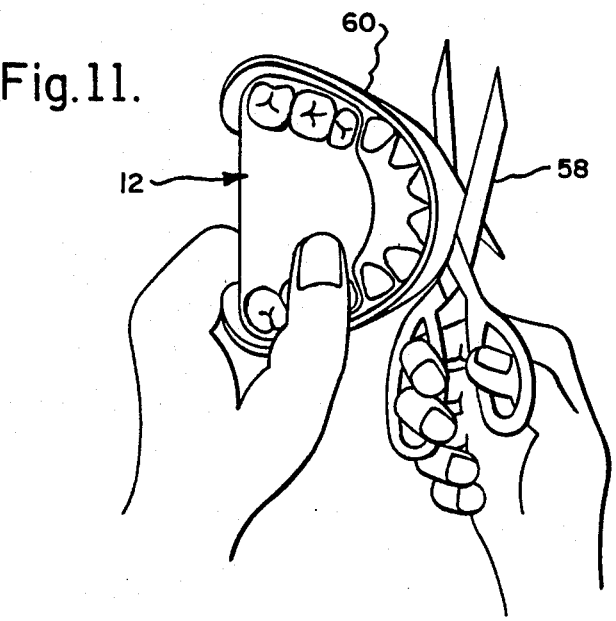
FIG. 11 is a perspective view of the positioner portion of the appliance being trimmed to a desired shape.

Once the positioner portion material 60 is cured, the model 50 is separated from both the positioner portion material 60 and the splint portion 16, and the positioner portion material 60 is pulled from the splint portion 12 for finishing the positioner portion 14. By way of example and as shown in FIG. 11, the positioner portion 14 is finished or trimmed by means of scissors 58 and its edges are smoothed by flame blowing with an alcohol torch. Commonly, the finished positioner portion 14 resembles a mouthguard or a common orthodontic tooth positioner.

As mentioned earlier, the end sections 30,32(FIG. 3) of the positioner portion 14 and the teeth-engaging parts 18,20 of the splint portion 12 have surfaces which can be meshed or mated together to releasably join the portions 12 and 14 so that the appliance 10 can be worn as a two-layered appliance with no need for adhesive therebetween. If, however, adhesive is desired to be used to bond the splint portion 12 and positioner portion 14 together, adhesive is applied to at least one of the splint or positioner portions 12 or 14 in the region thereof intended to engage the other portion 14 or 12, and the splint and positioner portions 12 and 14 are then firmly pressed together to bond the portions 12 and 14 together. The bonded portions 12 and 14 thereby comprise the finished appliance 10.

To utilize the appliance 10, a patient simply opens his mouth and positions the appliance 10 therein by pressing the appliance indentations and recesses over the teeth of the corresponding dental arch for which the appliance 10 was designed.

Figure 14:
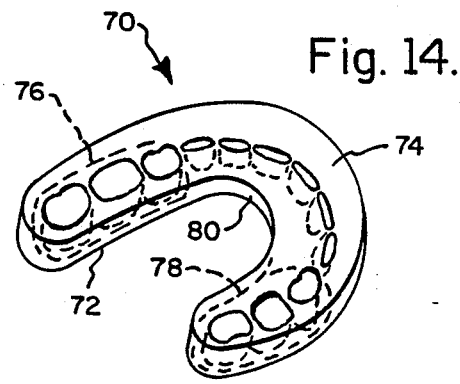
FIG. 14 is a perspective view of an alternative embodiment of an anchor appliance in accordance with the apparatus of the present invention.

It will be understood that numerous modifications and substitutions can be had to the aforedescribed embodiments without departing from the spirit of the invention. For example, although the appliance 10 of FIGS. 1–3 has been shown and described as constructed for positioning on the maxillary arch of a patient, an appliance in accordance with the apparatus of this invention can be constructed for use on the mandibular, or lower arch of the patient. For example, there is shown in FIG. 14 an alternative embodiment 70 of an anchor appliance for repositioning anterior teeth of the mandibular arch. The appliance 70 includes a split portion 72 having teeth engaging parts 76,78 for attachment to preselected molars on opposite sides of the mandibular arch and elastomeric positioner portion 74 in a form of a mouthguard for closely receiving the anterior of the mandibular arch. The splint portion 72 further includes a tissue-engaging part 80 joining the teeth-engaging parts 76,78 and which is so shaped to conform generally with the curvature of the gum tissue located inside the mandibular arch so that when positioned therein, the splint portion 72 fits comfortably between the gum tissue and the base of the tounge. Accordingly, the aforedescribed embodiments are intended for the purpose of illustration and not as limitation.

We claim:

1. An orthodontic anchor appliance for repositioning anterior teeth of a patient comprising:
   a relatively hard splint portion securable about and to preselected ones of the patient's posterior teeth positioned on opposite sides of the mouth and arranged in the corresponding one of the upper or lower dental arch containing the anterior teeth desired to be repositioned; and
   an elastic positioner portion joined to said splint portion and securable when in a flexed condition to preselected ones of the anterior teeth so that when said appliance is operatively positioned within the mouth of a patient so that the splint portion is operatively secured about the preselected ones of the posterior teeth and the positioner portion is operatively secured to the preselected ones of the anterior teeth, the elastic positioner portion acts between the splint portion and the anterior teeth to urge the anterior teeth toward a preselected position.

2. An appliance as defined in claim 1 wherein said splint portion includes two teeth-engaging parts positionable on opposite sides of the corresponding arch and adapted to closely receive the preselected ones of the posterior teeth and a tissue-engaging part joining the teeth-engaging parts to one another.

3. An orthodontic anchor appliance for repositioning anterior teeth of a patient comprising:
   a relatively hard splint portion securable to preselected ones of the patient's posterior teeth positioned on opposite sides of the mouth and arranged in the corresponding one of the upper or lower dental arch containing the anterior teeth desired to be repositioned, said splint portion including two teeth-engaging parts positionable on opposite sides of the corresponding arch and a tissue-engaging part joining the teeth-engaging parts to one another, each teeth-engaging part of the splint portion including means defining a recess shaped generally complementary to the crowns of the posterior teeth to which the teeth-engaging part is securable so that when the teeth-engaging parts are operatively secured to the posterior teeth, the posterior teeth are closely received by the recesses of the teeth-engaging parts; and
   an elastic positioner portion joined to said splint portion and securable when in a flexed condition to preselected ones of the anterior teeth so that when said appliance is operatively positioned within the mouth of a patient, the elastic positioner acts between the splint portion and the anterior teeth to urge the anterior teeth toward a preselected position.

4. An appliance as defined in claim 2 wherein said tissue-engaging part is adapted to lie in overlying relationship with tissue located inside the patient's mouth and includes means defining surfaces shaped generally complementary to the surface of tissue intended to be overlain thereby so that when the appliance is operatively positioned with the patient's mouth, said tissue-engaging part fits comfortably within the mouth.

5. An appliance as defined in claim 1 wherein said elastic positioner portion has a section which is in overlying relationship and mates with a section of said splint portion so that said splint and positioner portions are held together by the mated relationship.

6. An orthodontic anchor appliance for repositioning anterior teeth of a patient comprising:

a relatively hard splint portion securable to preselected ones of the patient's posterior teeth positioned on opposite sides of the mouth and arranged in the corresponding one of the upper or lower dental arch containing the anterior teeth desired to be repositioned; and an elastic positioner portion joined to said splint portion and securable when in a flexed condition to preselected ones of the anterior teeth so that when said appliance is operatively positioned within the mouth of a patient, the elastic positioner portion acts between the splint portion and the anterior teeth to urge the anterior teeth toward a preselected position, said elastic positioner portion including a teeth-engaging section including means defining an indentation including an inner surface shaped generally complementary to the crowns of the anterior teeth to which the positioner portion is securable when the anterior teeth are positioned in a preselected position so that when said appliance is operatively positioned within the mouth and about the anterior teeth, the anterior teeth are closely received by the indentation of the teeth-engaging section.

7. A method of constructing an anchor appliance for repositioning anterior teeth of a patient comprising the steps of:

providing a dental model formed from an impression of the corresponding one of the upper or lower dental arch of the patient containing the anterior teeth desired to be repositioned;

repositioning portions of the dental model simulating anterior teeth to a preselected position so as to provide a diagnostic model of the patient's dental arch when the anterior teeth therein are oriented in a preselected position;

shaping a hardenable material, when in a pliable condition, in conformity with portions of the diagnostic model simulating mouth tissue and a posterior teeth so that a first part of the pliable, hardenable material conforms to the shape of a preselected one of the patient's posterior teeth positioned on one side of the dental arch, a second part of the pliable, hardenable material conforms to the shape of a preselected one of the patient's posterior teeth positioned on the other side of the dental arch and a third part of the pliable, hardenable material joins said first and second parts and conforms to the shape of mouth tissue extending between the preselected posterior teeth positioned on opposite sides of the dental arch;

permitting the hardenable material to harden to form a splint portion of the appliance;

shaping a curable elastomeric material, when in a pliable condition, in conformity with at least a section of the splint portion and a portion of the diagnostic model simulating the repositioned anterior teeth; and permitting the elastomeric material to cure to a resiliently flexible condition so as to form an elastic positioner portion of the appliance and so that when the appliance is operatively positioned within the mouth of the patient so that the splint portion is closely fitted about the preselected ones of the posterior teeth and the positioner portion is closely fitted and in a flexed condition about the preselected ones of the anterior teeth, the splint portion is firmly anchored to the posterior teeth and the positioner portion acts between the splint portion and anterior teeth to urge the anterior teeth toward the preselected position.

8. The method of claim 7 wherein said step of repositioning portions of the dental model simulating anterior teeth includes the steps of cutting the anterior teeth from the dental model and resetting them within the remainder of the model in a prescribed position.

9. The method of claim 7 wherein said step of shaping a hardenable material includes the steps of applying the hardenable material about said tissue and posterior teeth-simulating portions of the diagnostic model and shaping the hardenable material about said tissue and posterior teeth-simulating portions.

10. The method of claim 7 wherein said step of permitting the hardenable material to harden to form a splint portion is followed by the steps of removing the splint portion from the diagnostic model, finishing the splint portion and replacing the splint portion upon a diagnostic model prior to the step of shaping the curable elastomeric material.

11. The method of claim 10, wherein the diagnostic model is a first diagnostic model said, said step of repositioning so as to provide the first diagnostic model is followed by a step of duplicating the first diagnostic model so as to provide a second diagnostic model, and said step of replacing the splint portion operatively positions the splint portion upon the second diagnostic model.

12. The method of claim 7 wherein the step of shaping the curable elastomeric material includes the steps of applying the elastomeric material to and shaping the elastomeric material about said section of the splint portion and said portion of the diagnostic model simulating the repositioned anterior teeth.

13. The method of claim 12 wherein said step of permitting the pliable elastomeric material to cure so as to form a positioner portion of the appliance is followed by the steps of removing the positioner portion from the diagnostic model and finishing the positioner portion.

14. The method of claim 7 wherein said step of permitting the pliable elastomeric material to cure so as to form a positioner portion is followed by the step of bonding the positioner and splint portions together.

15. The method of claim 14 wherein the step of bonding includes the step of spreading an adhesive over at least one of the surfaces of the splint and positioner portion which are intended to engage one another when operatively bonded together and positioning the splint and positioner portion in operative engaging relationship to securely bind the splint and positioner portions.

16. A method of repositioning anterior teeth of a patient including the steps of:

providing an orthodontic anchor appliance having a relatively hard splint portion and an elastic positioner portion joined to the splint portion, said splint portion being securable to preselected ones of the patient's posterior teeth positioned on opposite sides of the mouth and arranged in the corresponding one of the upper or lower dental arch containing the anterior teeth desired to be repositioned, said elastic positioner portion being securable when in a flexed condition to preselected ones of the anterior teeth so that when said appliance is operatively positioned within the mouth of a patient, the elastic positioner acts between the splint portion and the anterior teeth to urge the anterior teeth toward a preselected position; and positioning the anchor appliance within the patient's mouth so that the splint portion is secured to the posterior teeth and the elastic positioner portion acts between the splint portion and the anterior teeth to urge the anterior teeth toward a preselected position.

17. The method of claim 16 wherein said splint portion includes two teeth-engaging parts positionable on opposite sides of the corresponding arch and adapted to closely receive the preselected ones of the posterior teeth and said step of positioning the anchor appliance within the patient's mouth closely fits said splint portion about the preselected ones of the posterior teeth.

18. The method of claim 16 wherein said elastic positioner portion includes a teeth-engaging section including means adapted to closely receive the preselected ones of the anterior teeth when said preselected ones of the anterior teeth are positioned in a preselected orientation and said step of positioning the anchor appliance within the patient's mouth closely fits said positioner teeth-engaging section about said preselected ones of the anterior teeth.

19. The method of claim 16 is wherein the step of providing an orthodontic appliance includes the steps of:

providing a dental model formed from an impression of the corresponding one of the upper or lower dental arch of the patient containing the anterior teeth desired to be repositioned; and repositioning portions of the dental model simulating anterior teeth to a preselected position so as to provide a diagnostic model of the patient's dental arch when the anterior teeth therein are oriented in a preselected position;

shaping a hardenable material, when in a pliable condition, in conformity with portions of the diagnostic model simulating mouth tissue and posterior teeth so that a first part of the pliable, hardenable material conforms to the shape of a preselected one of the patient's posterior teeth positioned on one side of the dental arch, a second part of the pliable, hardenable material conforms to the shape of a preselected one of the patient's posterior teeth positioned on the other side of the dental arch and a third part of the pliable hardenable material joins said first and second parts and conforms to the shape of mouth tissue extending between the preselected posterior teeth positioned on opposite sides of the dental arch;

permitting the hardenable material to harden to form the splint portion of the appliance;

shaping a curable elastomeric material, when in a pliable condition, in conformity with at least a section of the splint portion and a portion of the diagnostic model simulating the repositioned anterior teeth; and permitting the elastomeric material to cure to a resiliently flexible condition so as to form the elastic positioner portion of the appliance.

* * * * *